United States Patent [19]

Bertleff et al.

[11] Patent Number: 4,600,726

[45] Date of Patent: Jul. 15, 1986

[54] PREPARATION OF ETHYLENE GLYCOL

[75] Inventors: Werner Bertleff, Viernheim; Franz-Josef Müller, Wachenheim; Rudolf Kummer, Frankenthal; Wolfgang Harder, Weinheim, all of Fed. Rep. of Germany

[73] Assignee: BASF Aktiengesellschaft, Ludwigshafen, Fed. Rep. of Germany

[21] Appl. No.: 758,293

[22] Filed: Jul. 24, 1985

[30] Foreign Application Priority Data

Jul. 24, 1984 [DE] Fed. Rep. of Germany ....... 3427138

[51] Int. Cl.⁴ ............................................. C07C 27/06
[52] U.S. Cl. ..................................... 518/701; 502/152
[58] Field of Search .......................................... 518/701

[56] References Cited

U.S. PATENT DOCUMENTS 3,878,290 4/1975 Walker et al. .
3,929,969 12/1975 Brown .
3,974,259 8/1975 Brown .

Primary Examiner—Howard T. Mars
Attorney, Agent, or Firm—John H. Shurtleff

[57] ABSTRACT

Ethylene glycol is prepared from carbon monoxide and hydrogen under superatmospheric pressure and at an elevated temperature in the presence of a rhodium-containing catalyst together with a cobalt catalyst, the molar ratio of rhodium to cobalt being from about 20:1 to 60:1.

4 Claims, No Drawings

PREPARATION OF ETHYLENE GLYCOL

The present invention relates to an improved process for the preparation of ethylene glycol from carbon monoxide and hydrogen under superatmospheric pressure and at elevated temperature, in the presence of a rhodium-containing catalyst.

Apart from the improvement according to the present invention, the said process is generally known from numerous publications. In particular, there have already been recommended for this so-called direct synthesis of lower alcohols from CO and $H_2$ (in which, in addition to the principally desired ethylene glycol, methanol and ethanol are formed, inter alia), catalysts which contain two or three different metals, including rhodium conjointly with cobalt in the form of the following carbonyl complexes (referred to as clusters)

$CoRh_{12}(CO)_{30}$ $[Co_yRh_{12-y}(CO)_{30}]_3M_2$ y=1-11; M=trivalent metal $[Co_yRh_{12-y}(CO)_{30}]M_2'$ M'=inter alia, monovalent rhodium as disclosed in U.S. Pat. Nos. 3,878,290, 3,929,969 and 3,974,259, respectively.

As may be seen from these formulae, the molar ratio of rhodium to cobalt is not more than 13:1.

However, the yields of ethylene glycol achievable with such clusters under various conditions prove unsatisfactory. Accordingly, it is the object of the present invention to improve these yields.

We have found that this object is achieved by an improved process for the preparation of ethylene glycol from carbon monoxide and hydrogen under superatmospheric pressure and at an elevated temperature, in the presence of a rhodium-containing catalyst, wherein the rhodium catalyst is used together with a cobalt catalyst, the molar ratio of rhodium to cobalt being from about 20:1 to 60:1.

Since it is not necessary for the rhodium and cobalt to form a defined carbonyl, complex, the two metals can be employed separately, namely either in the form of their pure carbonyl complexes such as $Co_2(CO)_8$, $Co_4(CO)_{12}$, $Rh_4(CO)_{12}$ and $Rh_6(CO)_{16}$, or in the form of other complexes, for example with acetylacetone, or in the form of salts or oxides such as cobalt acetate, cobalt carbonate, cobalt nitrate, rhodium chloride, rhodium acetate and rhodium oxide, since in each case the active complexes form in situ.

In what way ethylene glycol is formed from the structural units CO and $H_2$ is not known precisely, but it can be regarded as established that several reactions participate, a possible reaction sequence being the formation of formaldehyde or of a metal formyl complex, oxo-reaction to give the glycol aldehyde, and hydrogenation of the latter. In each of these steps, undesirable side-reactions are possible, for example hydrogenation of formaldehyde to methanol, as well as other reactions (for example homologization) which lead to ethanol, and presumably a single catalyst is not capable of favoring the desired direction of the overall reaction sequence. However, this is achieved satisfactorily by the use, according to the invention, of two different catalysts, namely based on rhodium and based on cobalt respectively, specifically in the range of molar ratios stated, an Rh/Co ratio of from 25:1 to 30:1 being particularly advisable in most cases.

Of course the ethylene glycol yield also depends on other reaction parameters, such as the pressure, the temperature, the rhodium concentration and the reaction medium, but, from out observations to date, it is characteristic of the process according to the invention that the additional presence of the cobalt catalyst under otherwise identical conditions in every case leads to higher yields of ethylene glycol than those obtained without the cobalt catalyst.

The total pressure is advantageously 300-3,000 bar, preferably 650-2,000 bar. The partial pressure of carbon monoxide is preferably from 20 to 80%, especially from 30 to 60%, of the total pressure.

Good results are achieved at 180°–280° C., the range of 200°–240° C. being generally preferable.

The rhodium concentration in the reaction medium can in principle be whatever is desired, since it essentially only influences the reaction velocity and hence the space-time yield. Satisfactory space-time yields are as a rule achieved at concentrations of 0.05–0.3% by weight of Rh; higher concentrations produce no significant further economic advantages, while at lower concentrations, say down to 0.01% by weight, the reaction slows down correspondingly.

A suitable reaction medium is, in principle, any inert organic liquid, ie. for example, a hydrocarbon such as toluene, xylene and cyclohexane, an ether, such as one of the monoalkyl, dialkyl, monoaryl and diaryl ethers of monoethylene glycol, diethylene glycol, triethylene glycol and tetraethylene glycol, an alcohol such as methanol, ethanol, propanol or cyclohexanol, and a sulfone, such as sulfolan.

Particularly suitable media are open-chain and cyclic tetraalkylureas. Lactones and N-alkyl- and N-aryl-pyrrolidones. Among these solvents, N-methylpyrrolidone, 1,5-dimethylpyrrolid-2-one and 1,3-dimethylimidazolid-2-one have proved particularly suitable.

Furthermore it is also advisable in the present case to carry out the reaction in the presence of an open-chain or cyclic tertiary amine, eg. N-methylmorpholine, since such compounds enter the catalysts as ligands, and, as is known, increase their stability. The amount of such compounds is preferably about 1–50 moles per mole of the central atoms Rh and Co.

The reaction can be carried out batchwise or continuously, in accordance with the customary techniques. Advantageously, the reaction mixture is worked up by distillation. The catalyst-containing residue thereby obtained can be used, together with the solvents, for further reaction batches or can, in continuous operation, be recycled to the synthesis stage.

The product obtained consists principally of ethylene glycol accompanied by methanol, ethanol and small amounts of other alcohols.

EXAMPLE 1

A solution of 100 ml of 1,3-dimethylimidazolid-2-one, 0.5 g of $Rh(CO_2)$.acetylacetone ($=1.9$ mol of Rh), 0.94 g (9.3 mmol) of N-methylmorpholine and $Co_2(CO)_8$ corresponding to Rh/Co molar ratio q was reacted for 6 hours at 240° C. and 650 bar with an equimolar $CO/H_2$ mixture.

Analysis by gas chromatography of the reaction mixture gave the results shown in the table below.

| Experiment | q | Yield in g of ethylene glycol | methanol | ethanol |
| --- | --- | --- | --- | --- |
| comparative | | | | |
| a | 1 | 6.82 | 4.20 | 0.94 |
| b | 2.5 | 7.07 | 4.57 | 1.87 |
| c | 10 | 7.99 | 3.46 | 0.61 |
| d | ∞ (without Co) | 6.13 | 2.38 | 0.36 |
| according to the invention | | | | |
| e | 20 | 8.29 | 3.93 | 0.81 |
| f | 25 | 8.93 | 4.42 | 1.00 |
| g | 30 | 8.66 | 3.65 | 0.66 |
| h | 41 | 8.84 | 3.91 | 0.82 |
| i | 47 | 9.14 | 3.58 | 0.63 |

The yields of ethylene glycol in Experiments (e)–(i) according to the invention are about 4–14% higher than in Experiment (c).

EXAMPLE 2

15 ml of a solution of 0.5 g (1.9 mmol of Rh) of $Rh(CO)_2$.acetylacetone, 0.94 g (9.3 mmol) of N-methylpyrrolidone, 100 ml of 1,5-dimethylpyrrolid-2-one and $Co_2(CO)_8$ corresponding to an Rh/Co molar ratio q were reacted with an equimolar $CO/H_2$ mixture for 6 hours at 230° C. under a pressure of 1,500 bar.

According to analysis by gas chromatography, the reaction mixture contained 10.9% by weight of ethylene glycol if q was 25, and only 4.1% by weight of ethylene glycol if q was 1.4.

EXAMPLE 3

Using the conditions of Example 1, but with 0.75 g (2.9 mmol of Rh) of the rhodium compound and 1.41 g of N-methylmorpholine, 12.85 g of ethylene glycol were formed if q was 22 and only 6.55 g if q was 1.2.

We claim:

1. In a process for the preparation of ethylene glycol from the reaction of carbon monoxide and hydrogen in an inert organic liquid under superatmospheric pressure and at an elevated temperature in the presence of a rhodium-containing catalyst, the improvement which comprises carrying out said reaction with the rhodium catalyst in combination with a cobalt catalyst, the molar ratio of rhodium to cobalt being from about 20:1 to 60:1.

2. An improved process as claimed in claim 1 wherein the ratio of rhodium to cobalt is about 25:1 to 30:1.

3. An improved process as claimed in claim 1 wherein the reaction is carried out in the presence of an open-chain or cyclic tertiary amine in an amount of about 1 to 50 moles per mole of the rhodium and cobalt atoms.

4. An improved process as claimed in claim 1 wherein the reaction is carried out at a total pressure of 300 to 3,000 bar, a carbon monoxide partial pressure of 20 to 80% of the total pressure and a temperature of 180° to 280° C.

* * * * *